(12) United States Patent
Foster

(10) Patent No.: US 8,560,087 B2
(45) Date of Patent: Oct. 15, 2013

(54) MEDICAL DEVICE LEAD INCLUDING A ROTATABLE COMPOSITE CONDUCTOR

(75) Inventor: Arthur J. Foster, Centerville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/316,130

(22) Filed: Dec. 9, 2011

(65) Prior Publication Data
US 2012/0083865 A1 Apr. 5, 2012

Related U.S. Application Data

(63) Continuation of application No. 12/189,571, filed on Aug. 11, 2008, now Pat. No. 8,112,160.

(60) Provisional application No. 61/013,786, filed on Dec. 14, 2007.

(51) Int. Cl.
*A61N 1/05* (2006.01)
(52) U.S. Cl.
USPC .......................................................... 607/127
(58) Field of Classification Search
CPC .............. A61N 1/3752; A61N 1/0573
USPC .......................................... 607/126, 127, 131
See application file for complete search history.

(56) References Cited

U.S. PATENT DOCUMENTS

| | | | |
|---|---|---|---|
| 3,890,977 A | 6/1975 | Wilson | |
| 4,365,639 A | 12/1982 | Goldreyer | |
| 4,386,615 A | 6/1983 | Sowton | |
| 4,437,474 A * | 3/1984 | Peers-Trevarton | 607/119 |
| 4,608,986 A | 9/1986 | Beranek et al. | |
| 4,628,943 A | 12/1986 | Miller | |
| 4,886,074 A | 12/1989 | Bisping | |
| 5,251,643 A | 10/1993 | Osypka | |
| 5,300,108 A * | 4/1994 | Rebell et al. | 607/127 |
| 5,330,523 A | 7/1994 | Campbell et al. | |
| 5,514,173 A * | 5/1996 | Rebell et al. | 607/127 |
| 5,522,874 A * | 6/1996 | Gates | 607/127 |
| 5,545,201 A | 8/1996 | Helland et al. | |
| 5,716,390 A * | 2/1998 | Li | 607/127 |
| 5,968,087 A * | 10/1999 | Hess et al. | 607/127 |
| 6,108,582 A * | 8/2000 | Fischer, Sr. | 607/127 |
| 6,269,272 B1 * | 7/2001 | Fischer, Sr. | 607/127 |
| 6,463,334 B1 * | 10/2002 | Flynn et al. | 607/127 |
| 6,606,522 B2 | 8/2003 | Schell | |
| 6,671,562 B2 | 12/2003 | Osypka et al. | |
| 6,687,550 B1 * | 2/2004 | Doan | 607/127 |

(Continued)

OTHER PUBLICATIONS

Adler et al., "Thin Bipolar Leads: A Solution to Problems with Coaxial Bipolar Designs," PACE 15, November Part II, 1992, pp. 1986-1990.

(Continued)

*Primary Examiner* — Allen Porter, Jr.
(74) *Attorney, Agent, or Firm* — Faegre Baker Daniels LLP

(57) ABSTRACT

A medical electrical lead includes a proximal connector including a rotatable portion and first and second co-radial conductors coupled to the rotatable portion and extending distally from the rotatable portion. An actuation member is coupled between an electrode and the first and second conductors such that rotating the rotatable portion of the proximal connector transmits torque through the co-radial first and second conductors to the actuation member and results in both rotational and linear motion of the electrode.

13 Claims, 3 Drawing Sheets

(56) References Cited

U.S. PATENT DOCUMENTS

| | | | |
|---|---|---|---|
| 6,701,191 B2 | 3/2004 | Schell | |
| 6,704,605 B2 * | 3/2004 | Soltis et al. | 607/127 |
| 6,717,056 B2 | 4/2004 | Rivelli et al. | |
| 6,813,521 B2 * | 11/2004 | Bischoff et al. | 607/122 |
| 6,819,959 B1 * | 11/2004 | Doan et al. | 607/127 |
| 7,212,870 B1 | 5/2007 | Helland | |
| 7,337,009 B2 | 2/2008 | Schell | |
| 7,840,283 B1 | 11/2010 | Bush et al. | |
| 8,112,160 B2 | 2/2012 | Foster | |
| 2002/0183822 A1 * | 12/2002 | Bodner | 607/122 |
| 2002/0188340 A1 * | 12/2002 | Bischoff et al. | 607/127 |
| 2004/0059396 A1 * | 3/2004 | Reinke et al. | 607/60 |
| 2004/0064176 A1 | 4/2004 | Min et al. | |
| 2004/0127967 A1 | 7/2004 | Osypka | |
| 2004/0147963 A1 | 7/2004 | Sommer et al. | |
| 2005/0246007 A1 * | 11/2005 | Sommer et al. | 607/127 |
| 2005/0267557 A1 | 12/2005 | Flynn et al. | |
| 2007/0038280 A1 * | 2/2007 | Bodner et al. | 607/128 |
| 2008/0109042 A1 | 5/2008 | Bodner et al. | |
| 2009/0099635 A1 | 4/2009 | Foster | |

OTHER PUBLICATIONS

Extended European Search Report Issued in EP Application No. 11158825, dated Jun. 8, 2011, 5 pages.

International Search Report and Written Opinion issued in issued in PCT/US2008/072789, mailed Nov. 17, 2008, 10 pages.

* cited by examiner

MEDICAL DEVICE LEAD INCLUDING A ROTATABLE COMPOSITE CONDUCTOR

RELATED APPLICATIONS

This application is a continuation of U.S. patent application Ser. No. 12/189,571, filed Aug. 11, 2008, and entitled FIXATION HELIX AND MULTIPOLAR MEDICAL ELECTRODE, and claims priority under 35 U.S.C. §119(e) to U.S. Provisional Patent Application No. 61/013,786 filed on Dec. 14, 2007, the entire contents of which are incorporated herein by reference.

TECHNICAL FIELD

The present invention relates to implantable medical devices for stimulating body tissues and/or sensing physiological attributes. More specifically, the invention relates to helical fixation electrodes used in such devices.

BACKGROUND

Various physiological functions can be managed and/or monitored using medical devices. Many such medical devices include fixation electrodes, where the fixation electrode is configured to both fix the medical device to a location in the body and also deliver an electrical signal to a target location within the body and/or sense an electrical signal at a target location within the body. For example, implantable medical devices have been used in association with cardiac rhythm management, which can include cardiac pacing, cardiac defibrillation, and/or cardiac therapy, among other procedures. Various designs for such fixation electrodes are known in the art. There exists a need for alternative designs for fixation electrodes that can be used in such medical devices.

SUMMARY

In one embodiment, a medical electrical lead includes a proximal connector including a rotatable portion and first and second co-radial conductors coupled to the rotatable portion and extending distally from the rotatable portion. An actuation member is coupled between an electrode and the first and second conductors such that rotating the rotatable portion of the proximal connector transmits torque through the co-radial first and second conductors to the actuation member and results in both rotational and linear motion of the electrode.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
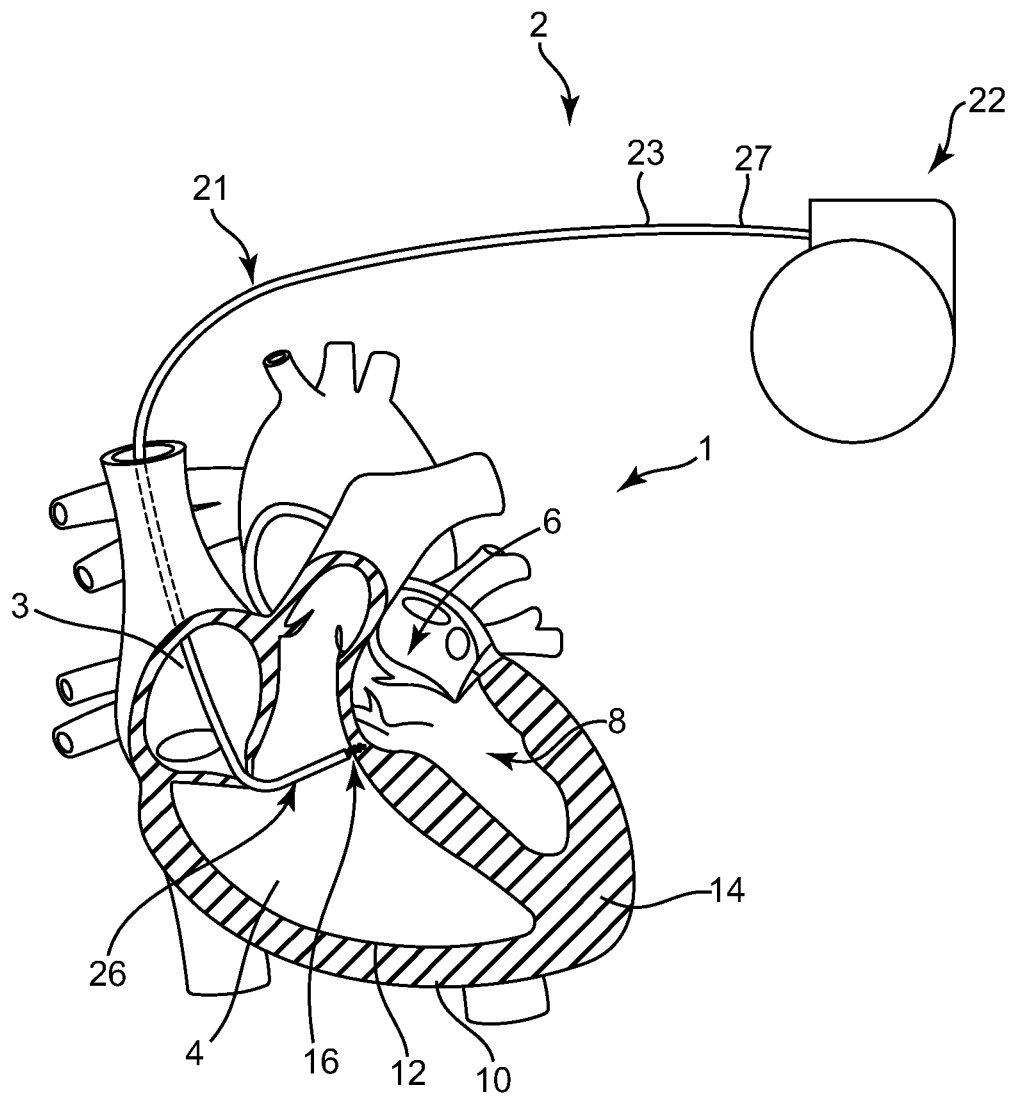
FIG. 1 shows an exemplary implantable medical device according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a combined cutaway view of a human heart 1 and a perspective view of an exemplary cardiac rhythm management (CRM) device 2. The heart 1 has a right atrium 3, a right ventricle 4, a left atrium 6, a left ventricle 8, an epicardium 10, an endocardium 12 and a myocardium 14. The CRM device 2 can be implanted at a site of interest 16, as further discussed below.

The CRM device 2 includes a lead 21 and a pulse generator 22. The lead 21 has a lead body 23 with a distal end portion 26 and a proximal end portion 27. The lead 21 also has a composite helical electrode 30 (shown in detail in FIG. 2) disposed on the lead body distal end portion 26.

The composite helical electrode 30 operates as a fixation helix, and the composite helical electrode 30 is configured to be implantable in a portion of the heart 1 at the target site 16. As shown in FIG. 1, at least a portion of the composite helical electrode 30 is implanted through the endocardium 12 and into the myocardium 14 at the target site 16. In FIG. 1, the target site 16 is at or near the location of the His bundle of the heart 1. In other embodiments, the lead 21 can be implanted at other locations in the heart 1. For example, the lead 21 can be implanted at other locations in the right ventricle 4, or in the right atrium 3, the left atrium 6 or the left ventricle 8.

In addition, the lead 21 can be implanted through the epicardium 10 and into the myocardium 14. For example, the lead 21 can be implanted through the epicardium 10 and into the myocardium 14 of the right atrium 3, the right ventricle 4, the left atrium 6 or the left ventricle 8. In such cases, the lead 21 can be delivered through the circulatory system of the heart to the location of interest, or it can be implanted in the epicardium 10 by gaining access to the pericardial space.

CRM devices that comprise two or more electrodes can be multipolar. In some multipolar systems, two electrodes function as the two poles of the CRM device. This is often called a "bipolar" system. In other multipolar systems, one of the electrodes of the CRM device acts as one pole of an electrical system, and the second pole of the electrical system can be located remotely from the electrode. For example, the second pole of the electrical system can be located on a pulse generator, or it can be located in another portion of the patient's body or on the surface of the patient's body. The CRM device can be programmed to sense which of the electrodes most efficiently stimulates tissues. The CRM device can then use the most efficient electrode as one pole of the device and the remote pole as the second pole of the device. Various configurations for multipolar devices are known in the art.

When the CRM device is energized, an electrical potential can be created between the two electrical poles of the device. This potential can create an electrical field and, in some cases, can create a current between the poles. When this electrical field or current is sufficiently strong, and when myocardial cells are disposed within the field or current, the myocardial cells can become depolarized, which leads to the contraction of the heart muscle. In addition, myocardial cells have the ability to propagate this electrical signal, causing depolarization of adjacent myocardial cells. This self propagation within the myocardium allows a target area of the heart to contract upon the stimulation of only a portion of the target area.

Further, when a CRM device is disposed near a nerve or other specialized tissues, for example the AV node or the His bundle, stimulation of the nerve or specialized tissues can cause a signal to be sent to one or more regions of myocardial cells. Again, as mentioned above, the myocardial cells then have the ability to self-propagate this electrical signal.

Alternatively, or in addition to stimulating the cardiac tissues, in some embodiments the electrodes of the CRM device can be configured to sense certain physiological attributes of the heart. For example, the heart's natural electrical signals can be received by an electrode and transmitted to a remote location (e.g., the pulse generator 22). In discussing embodiments of this invention, reference will be made primarily to electrodes stimulating body tissues. However, those of ordinary skill in the art will recognize that some or all of these electrode configurations could also be used to receive electrical signals from the body.

Figure 2:
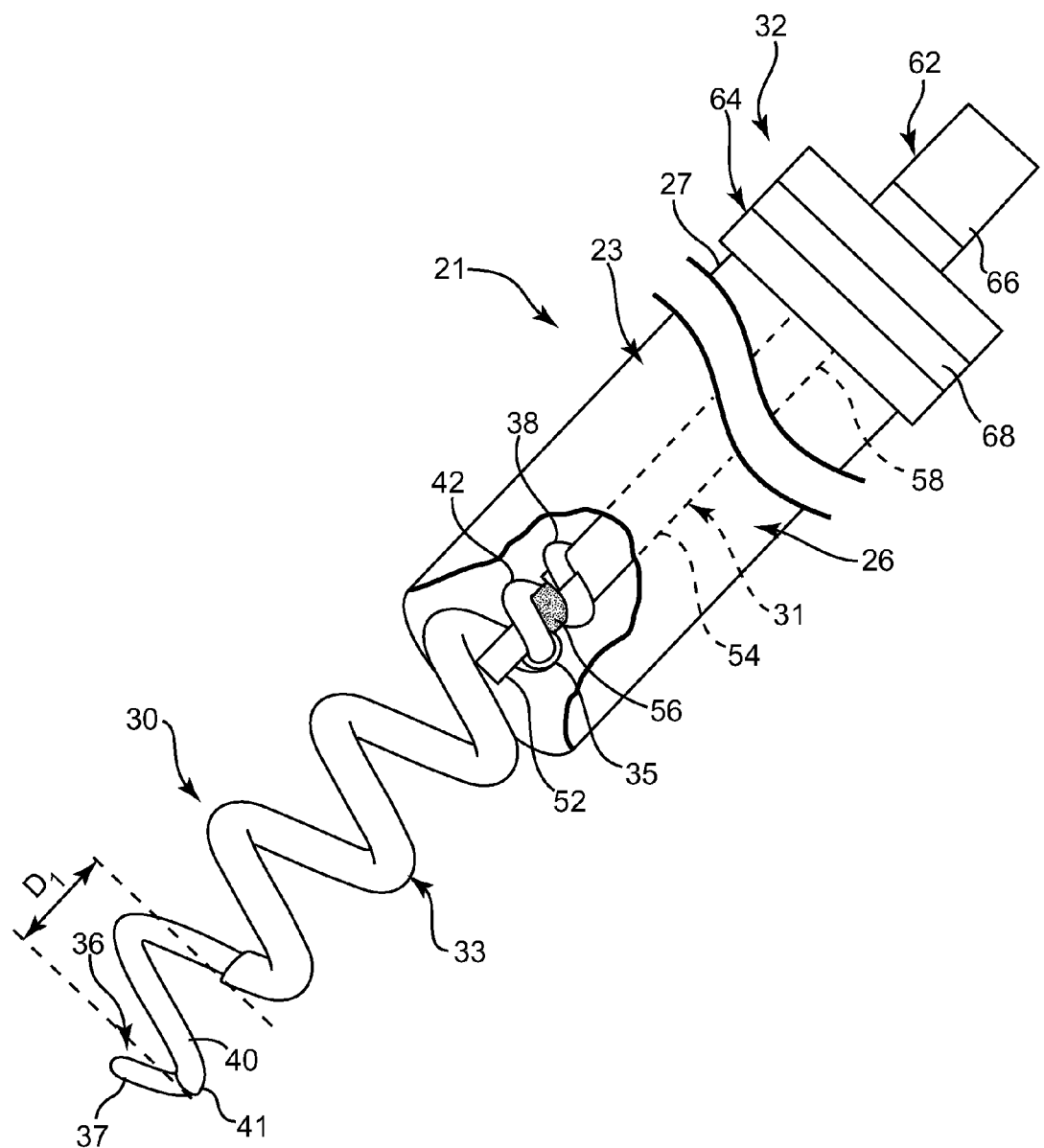
FIG. 2 shows a longitudinal cross-sectional view of a medical device lead according to embodiments of the present invention.

FIG. 2 is a partial cut-away view of the lead 21 according to embodiments of the present invention. The lead 21 includes the lead body 23, the composite helical electrode 30, a composite conductor 31 and a proximal connector 32. The composite conductor 31 is disposed within and extends through at least a portion of the lead body 23. The composite conductor 31, as described further below, electrically couples electrodes 33, 36 of the composite helical electrode 30 to the proximal connector 32. The proximal connector 32 is shaped and configured to facilitate the mechanical and electrical connection of the lead 21 to the pulse generator 22 or other device.

The composite helical electrode 30 comprises a first tubular shaped electrode 33, a second electrode 36 disposed within the first electrode 33, and an electrode insulating layer 40 radially disposed between the first and second electrodes 33, 36 in order to insulate the first and second electrodes 33, 36 from one another.

At least a portion of the first electrode 33 comprises an exposed surface that can act as a first pole of the composite helical electrode 30. As shown in FIG. 2, a distal portion of the first electrode 33 is exposed (i.e., uncovered by insulative material), with a proximal portion being electrically insulated from the surrounding environment by the lead body 23. A proximal portion can also be insulated by an outer electrode insulating layer (not shown).

The electrode insulating layer 40 extends distally from a distal end of the first electrode 33, and the second electrode 36 extends distally from an electrode insulating layer distal end 41. A portion of the second electrode distal end 37 that extends distally from the electrode insulating layer 40 forms a distal exposed surface of the second electrode 36 and also forms a distal end of the composite helical electrode 30.

The second electrode distal exposed surface acts as a second pole of the composite helical electrode 30. The electrode insulating layer 40 extends distally from the first electrode 33 a sufficient distance in order to electrically isolate the exposed surfaces of the first and second electrodes 33, 36. As such, the insulating layer 40 terminates between the distal end of the first electrode 33 and the second electrode distal end 37. The distance between the exposed surfaces of the first and second electrodes 33, 36 is shown as $D_1$. This distance is measured along an axis extending along the lead body 23. In one embodiment, the distance $D_1$ is about 1.5 mm. In other embodiments, $D_1$ is between about 1 mm and about 2 mm, between about 1 mm and about 3 mm, or between about 1 mm and about 4 mm.

A composite helical electrode proximal end is coupled to the composite conductor 31. The composite conductor 31 electrically connects the electrodes 33, 36 of the composite helical electrode 30 to the proximal connector 32. As such, the composite conductor 31 comprises two elongate conductors 52, 54. In the example shown in FIG. 2, the composite conductor 31 has a first inner conductor 52 disposed within a second outer, tubular conductor 54. A conductor insulating layer 56 is radially disposed between the two conductors 52, 54 in order to electrically isolate the two conductors 52, 54 from one another.

The first conductor 52 extends distally of both the conductor insulating layer 56 and the second conductor 54, forming a first distal outer surface of the composite conductor 31. The conductor insulating layer 56 extends distally from the distal end of the second conductor 54. In addition, a distal portion (i.e., the distal end) of the second conductor 54 defines a second distal outer surface of the composite conductor 31. The insulating layer 56 terminates between the distal ends of the first and second conductors 52, 54, electrically insulating the distal outer surfaces of the first and second conductors 52, 54 from one another.

In addition, a composite helical electrode proximal end portion defines proximal outer surfaces. For example, a proximal end 35 of the first electrode 33 comprises a first proximal outer surface of the composite helical electrode 30. As shown in FIG. 2, this first proximal outer surface can mechanically and electrically couple to the first distal outer surface of the first conductor 52. In the illustrated embodiment, the first proximal outer surface of the first electrode 33 is wrapped around the first distal outer surface of the first conductor 52 and/or the two outer surfaces can be crimped, brazed or welded to one another, or they can be coupled to one another in any other fashion known in the art.

Further, the insulating layer proximal end 42 extends proximally from the first electrode proximal end 35, and the second electrode proximal end 38 extends proximally from the insulating layer proximal end 42, forming a second proximal outer surface of the composite helical electrode 30. This second proximal outer surface is mechanically and electrically coupled to the distal outer surface of the second conductor 54. For example, the proximal outer surface of the second electrode 36 is wrapped around the distal outer surface of the second conductor 54 and/or the two outer surfaces can be crimped, brazed or welded to one another, or they can be coupled to one another in any other fashion known in the art.

As mentioned above, the insulating layer proximal end 42 extends proximally from the first electrode proximal end 35, and as such terminates between the first and second electrode proximal ends 35, 38, effectively insulating the proximal outer surfaces of the first and second electrodes 33, 36 from one another. As shown in the illustrative embodiment of FIG. 2, the portion of the electrode insulating layer proximal end 42 that extends proximally from the first electrode proximal end 35 is substantially coextensive with the portion of the conductor insulating layer 56 that extends distally from the distal end of the second conductor 54. In this way, the first electrode 33 and the first conductor 52 form an electrically conductive pathway that is electrically insulated from an electrically conductive pathway formed by the second electrode 36 and the second conductor 54.

In the illustrated embodiment, the connector 32 includes a connector pin 62 extending from a connector body 64. The connector pin 62 includes a first electrical contact 66 and the connector body 64 includes a second electrical contact 68. The composite conductor 31 extends through the lead body 23 from the lead body distal end portion 26 to the lead body proximal end portion 27. A composite conductor proximal end 58 is attached to the proximal connector 32. The first electrical contact 66 can be electrically coupled to one of the first and second conductors 52, 54 and the second electrical contact 68 can be electrically coupled to the other of the first and second conductors 52, 54. The proximal connector 32 is shaped and configured to be received within a port in the header of the pulse generator 22 shown in FIG. 1.

The composite conductor 31 extends through the lead body 23 in a straight (uncoiled), or substantially straight, configuration. In some embodiments, the composite conductor 31 can be coaxial within the lead body 23, although other configurations are possible. Further, the first conductor 52 is a core member of the composite conductor 31, and the first and second conductors 52, 54 and the conductor insulating layer 56 are arranged coaxially with respect to one another, although other configurations are possible. For example, in some embodiments the composite conductor 31 can comprise multiple coils, and the coils can be configured co-radially or co-axially. Examples of coiled composite conductors are further discussed below with respect to FIG. 3.

The combination of one of the contacts 66, 68, the first conductor 52 and the first electrode 33 forms a first electrically conductive pathway. This first electrically conductive pathway can be used to send electrostimulating signals to the first electrode 33 and/or to sense electrical signals that occur near the first electrode 33. Further, the combination of the other of the contacts 66, 68, the second conductor 54 and the second electrode 36 forms a second electrically conductive pathway. This second electrically conductive pathway can be used to send electrostimulating signals to the second electrode 36 and/or to sense electrical signals that occur near the second electrode 36. As mentioned above, the first and second electrically conductive pathways are electrically insulated from one another, and as such each of the electrically conductive pathways act as separate poles of the lead 21. As mentioned earlier, such a lead body 21 can be configured to function in various multipolar configurations.

The lead body 23 is formed around the composite conductor 31 and can extend from the proximal connector 32 distally to cover a proximal portion of the composite helical electrode 30. The lead body 23 can comprise any suitable biocompatible, flexible material, such as silicon, polyurethane, PTFE or other suitable materials. Further, the combination of the lead body 23 and the composite conductor 31 can facilitate transmission of torque from the lead body proximal end 27 to the lead body distal end 26. In turn, the torque can facilitate the implantation of the composite helical electrode 30 at a site of interest.

In embodiments such as those shown in FIG. 2, the lead 21 can be delivered through a delivery catheter, or by other methods known in the art. In other embodiments, the lead body 23 can have a stylet lumen (not shown) formed therethrough. As is known in the art, a stylet can be placed in the stylet lumen in order to facilitate delivery of the lead 21.

Also disclosed is a method of manufacturing the composite helical electrode 30. In the method, a composite billet can be formed which comprises a first tubular member corresponding to the first electrode 33 and an elongate member (e.g., a rod or wire) corresponding to the second electrode 36. An insulative material corresponding to the electrode insulating layer 40 can be disposed on the outer surface of the elongate member and/or on the inner surface of the first tubular member. The elongate member can be placed inside the first tubular member, forming the composite billet. In the alternative, or in addition, the material corresponding to the electrode insulating layer 40 can be provided by a second tubular member which can be placed between the elongate member and the first tubular member to form the composite billet.

The composite billet can then be drawn down to the desired dimensions, which can cause the different components of the composite billet to fuse together. The drawn composite billet can then be formed into a desired shape, for example a helical shape. Before or after being formed into a helix, the composite billet can be cut to length and portions of the electrode insulating layer 40 and the first electrode 33 can be removed in order to form the distal exposed surface and the proximal outer surface of the second electrode, as discussed above.

In another method of manufacturing the composite helical electrode 30, an elongate member (i.e., a wire or rod) corresponding to the second electrode 36 can be coated with an insulating material corresponding to the electrode insulating layer 40. The coating can be disposed on the elongate member by heat-shrinking a tubular member around the elongate member, by dipping the elongate member in a molten form of the insulative material, or by other methods known in the art. A tubular member corresponding to the first electrode 33 can then be disposed over the insulative material, forming an elongate composite member. Each of the individual components of the elongate composite member can have the helical shape of the composite helical electrode 30 before they are assembled to form the elongate composite member, or the elongate composite member can be formed into the helical shape after the elongate composite member is formed. The elongate composite member can be cut to length and portions of the electrode insulating layer 40 and the first electrode 33 can be removed in order to form the distal exposed surface and the proximal outer surface of the second electrode, as discussed above.

The first and second electrodes 33, 36 can comprise any conductive material that is suitably rigid to facilitate implantation of the composite helical electrode 30. For example, the first and second electrodes 33, 36 can comprise platinum, platinum alloys (i.e., platinum-iridium alloys), palladium, palladium alloys, MP35N, Stainless steel, titanium, and titanium alloys. The electrodes 33, 36 can also be partially or entirely coated, for example with an iridium-oxide coating. The electrode insulating layer can comprise any suitable insulative material, for example polyimide polyurethane, ETFE (e.g., Tefzel® ETFE) or composite materials (e.g., silicone/polyurethane composites).

As mentioned above, the composite conductor 31 can comprise a tubular member corresponding to the second conductor 54 and a core member corresponding to the first conductor 52. The composite conductor 31 can be manufactured in any suitable manner, including a drawing process similar to the drawing process discussed above with respect to the composite helical coil 30. In other embodiments, the composite conductor 31 can comprise an inner and outer coil, the inner coil corresponding to the first conductor 52 and the outer coil corresponding to the second conductor 54. These inner and outer coils can be insulated from one another, for example by the conductor insulating layer 56 or by disposing an insulating material on one or both of the coils. In addition, the coils corresponding to the first and second conductors 52, 54 can be disposed in a side-by-side manner, as shown below in FIG. 3. Additional information regarding composite conductors is disclosed in U.S. Patent Provisional Application No. 60/980, 351, entitled "Stimulation and Sensing Lead with Non-Coiled Wire Construction," filed on Oct. 16, 2007, which is incorporated herein in its entirety.

Figure 3:
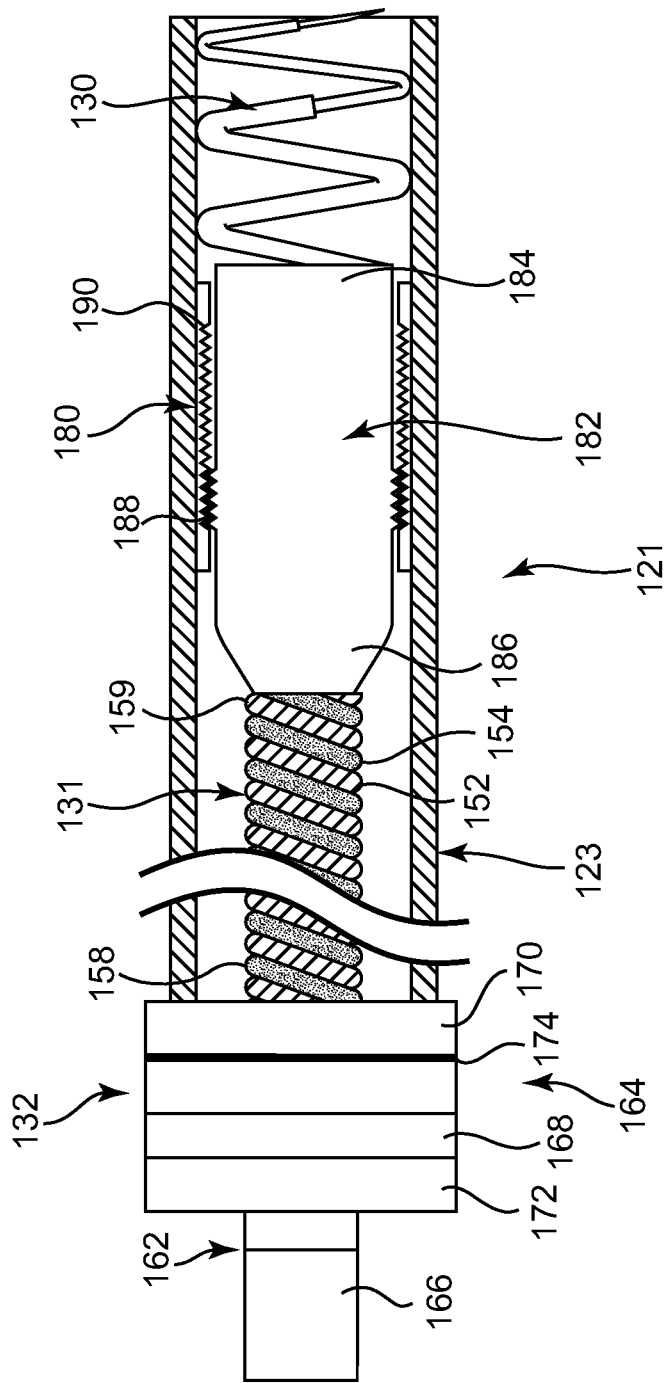
FIG. 3 shows a longitudinal cross-sectional view of another medical device lead according to embodiments of the present invention.

FIG. 3 is a cut-away view of another lead 121 according to embodiments of the invention. As shown, the lead 121 is overall similar to the lead 21, and includes a lead body 123 and a composite helical electrode 130. In the embodiment of FIG. 3, however, the electrode 130 is extendable/retractable. That is, in this embodiment, the composite helical electrode 130 can be rotated and extended with respect to the lead body 123, for example to facilitate implantation of the composite helical electrode 130.

As further shown in FIG. 3, the composite helical electrode 130 is coupled to an actuation mechanism 180, which in turn is coupled to a composite conductor 131. The composite conductor 131 extends proximally from the actuation mechanism 180 through the lead body 123 to a proximal connector 132.

The composite helical electrode 130 can be similar to the composite helical electrode 30 described above. The distal end is shaped and configured to function as a fixation helix, and the proximal end is rotatably and axially fixed to a portion of the actuation mechanism 180, as further described below.

The actuation mechanism 180 is configured to extend and retract the composite helical electrode 130. For example, the actuation mechanism 180 comprises a jack screw 182 with a distal end 184 and a proximal end 186. The jack screw 182 includes teeth 188 disposed thereon. As shown, the inner wall of the lead body 123 includes teeth 190, and the two sets of teeth 188, 190 are shaped and configured to mesh with one another such that, when the jack screw 182 is rotated, the jack screw 182 will move longitudinally with respect to the lead body 123. The composite helical electrode proximal end can be rotatably and axially fixed to the jack screw distal end 184, and as such actuating the jack screw 182 can cause the composite helical electrode 130 to rotate and move longitudinally. In addition, other mechanisms for rotatably and/or longitudinally actuating the composite helical electrode 130 are known in the art.

The composite conductor 131 has a proximal end 158 and a distal end 159. The composite conductor distal end 159 is rotatably and axially fixed to the jack screw proximal end 186. The composite conductor 131 facilitates the transmission of torque to the jack screw proximal end 186 from the proximal connector 132, as further described below. The composite conductor 131 comprises two or more coils 152, 154 in a co-radial configuration. As shown in FIG. 3, the coils 152, 154 are incorporated into the composite conductor in a side-by-side manner, and the coils can be insulated from one another by coating one or both of the coils with insulative material. In other embodiments, the coils 152, 154 can be disposed in a layered manner, for example with the first coil 152 disposed co-axially within the second coil 154.

In addition to transmitting torque from the proximal connector 132 to the jack screw 182, the coils 152, 154 also facilitate the transmission of electrical signals between the proximal connector 132 and the composite helical electrode 130. For example, the first coil 152 can extend into the jack screw 182 and attach to a first electrode of the composite helical electrode 130 and the second coil 154 can extend into the jack screw 182 and attach to a second electrode of the composite helical electrode 130. The coils 152, 154 can attach directly or indirectly to the first and second electrodes of the composite helical electrode 130.

As mentioned above, the composite conductor 131 mechanically couples the jack screw 182 to the proximal connector 132. The proximal connector 132 has a connector pin 162 and a connector body 164. In addition, the connector body 164 is divided into distal 170 and proximal 172 portions. The distal 170 and proximal 172 portions are rotatable with respect to one another, and interface at a rotatable interface 174. The connector body distal portion 170 is rotatably and longitudinally fixed to the lead body proximal end, while the connector body proximal portion 172 is rotatably and longitudinally fixed to the composite conductor proximal end 158. When the connector body proximal portion 172 is rotated with respect to the connector body distal portion 170, the composite conductor 131 transmits torque from the connector body proximal portion 172 to the jack screw 182, which causes the jack screw 182 to rotate. Rotation of the jack screw 182 causes rotational and longitudinal movement of the jack screw 182, and in turn rotational and longitudinal movement of the composite helical electrode 130. The rotational and longitudinal movement of the composite helical electrode 130 can be used to implant the composite helical electrode 130 at a site of interest. Further, as the jack screw 182 is extended, the coils 152, 154 of the composite conductor 131 stretch in order to accommodate the movement of the jack screw 182.

The proximal connector 132 also has two or more electrical contacts 166, 168. These contacts can be similar to the contacts 66, 68 described above with respect to FIG. 2.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations that fall within the scope of the claims, together with all equivalents thereof.

I claim:

1. A medical electrical lead comprising:
   an insulative lead body including a proximal portion and a distal portion;
   a proximal connector connected to the proximal portion of the insulative lead body, the proximal connector including a connector pin having a first electrical contact and a connector body having a second electrical contact, wherein the proximal connector has a rotatable portion that includes the connector pin and a portion of the connector body that has the second electrical contact, wherein the rotatable portion is rotatable with respect to the insulative lead body;
   first and second electrodes;
   a composite conductor comprising a first conductor electrically coupled to the first electrical contact of the connector pin and the first electrode to form a first electrical pathway and comprising a second conductor electrically coupled to the second electrical contact on the connector body and the second electrode to form a second electrical pathway, wherein the first and second conductors are co-radial and at least one of the first and second conductors comprises a coating of insulative material that insulates the first conductor from the second conductor; and
   an actuation member coupled between the first and second electrodes and the composite conductor such that rotating the rotatable portion of the proximal connector transmits torque through each of the first and second conductors of the composite conductor to the actuation member and results in both rotational and linear motion of the first and second electrodes.

2. The medical electrical lead of claim 1,
   wherein the actuation member includes first threads disposed on the outer surface thereof configured to mechanically interact with second threads on the inner surface of the lead body to convert rotational motion of the actuation member into linear motion of the actuation member such that rotating the rotatable portion of the proximal connector results in both rotational and linear motion of the first and second electrodes.

3. The medical electrical lead of claim 1, wherein the first and second conductors are both coil conductors.

4. The medical electrical lead of claim 3, wherein the coil conductors are disposed in a side-by-side configuration.

5. The medical electrical lead of claim 1, wherein at least one of the first and second electrodes has a sharpened distal end shaped and configured to pierce tissue.

6. The medical electrical lead of claim 1, wherein the actuation member comprises
a jack screw disposed in the insulative lead body, the jack screw having first threads disposed on an outer surface thereof configured to mechanically interact with second threads on an inner surface of the insulative lead body to convert rotational motion of the jack screw into linear motion of the jack screw such that rotating the rotatable portion of the proximal connector transmits torque through the first and second conductors to the jack screw and results in both rotational and linear motion of the first and second electrodes.

7. The medical electrical lead of claim 6, wherein the rotatable portion of the proximal connector is a proximal part of the proximal connector and a distal portion of the proximal connector is rotatably fixed with respect to the insulative lead body.

8. The medical electrical lead of claim 6, wherein the first and second conductors are both coil conductors.

9. The medical electrical lead of claim 6, wherein a distal end of the first and second conductors are coupled to the jack screw.

10. The medical electrical lead of claim 6, wherein at least one of the first and second electrodes has a sharpened distal end shaped and configured to pierce tissue.

11. The medical device lead of claim 6, wherein the first and second conductors are configured to stretch to accommodate rotational and linear movement of the jack screw.

12. A method of implanting a lead at a desired location in a patient comprising:
providing a lead having:
an insulative lead body including a proximal portion and a distal portion;
a proximal connector connected to the proximal portion of the insulative lead body, the proximal connector including a connector pin having a first electrical contact and a connector body having a second electrical contact, wherein the proximal connector has a rotatable portion that includes the connector pin and a portion of the connector body that has the second electrical contact, wherein the rotatable portion is rotatable with respect to the insulative lead body;
first and second electrodes;
a composite conductor comprising a first conductor electrically coupled to the first electrical contact of the connector pin and the first electrode to form a first electrical pathway and comprising a second conductor electrically coupled to the second electrical contact on the connector body and the second electrode to form a second electrical pathway, wherein the first and second conductors are co-radial and at least one of the first and second conductors comprises a coating of insulative material that insulates the first conductor from the second conductor; and
an actuation member coupled between the first and second electrodes and the composite conductor such that rotating the rotatable portion of the proximal connector transmits torque through each of the first and second conductors of the composite conductor to the actuation member and results in both rotational and linear motion of the first and second electrodes; and
rotating the rotatable portion of the proximal connector with respect to the insulative lead body to transmit torque through the first and second conductors to the actuation member and extend the first and second electrodes from the lead body and implant the lead at the desired location within the patient.

13. The method of claim 12, wherein a distal end of at least one of the first and second electrodes is sharpened and is configured to pierce tissue, and wherein tissue is pierced with the sharpened distal end as the first and second electrodes are extended from the lead body and implanted at the desired location.

* * * * *